United States Patent

Carter et al.

[11] Patent Number: 5,593,443
[45] Date of Patent: Jan. 14, 1997

[54] PROSTHETIC ANAL SPHINCTER

[75] Inventors: Kenneth B. Carter; Ian G. Finlay, both of Glasgow; William Richardson, Johnstone, all of United Kingdom

[73] Assignee: NPH Ltd., Onchan, Isle of Man

[21] Appl. No.: 551,052

[22] Filed: Oct. 31, 1995

Related U.S. Application Data

[63] Continuation of Ser. No. 117,181, filed as PCT/GB92/00349 Feb. 24, 1992, abandoned.

[30] Foreign Application Priority Data

Mar. 13, 1991 [GB] United Kingdom ............ 9105346
Sep. 14, 1991 [GB] United Kingdom ............ 9119685

[51] Int. Cl.⁶ ............................................. A61F 2/02
[52] U.S. Cl. ........................... 623/14; 128/DIG. 25; 600/31; 606/202
[58] Field of Search ............... 623/14; 128/DIG. 25, 128/843; 600/29–31, 37; 606/202, 203, 197

[56] References Cited

U.S. PATENT DOCUMENTS

| 3,675,656 | 7/1972 | Hakim | 606/202 X |
| 3,831,583 | 8/1974 | Edmunds et al. | 606/202 X |
| 3,866,611 | 2/1975 | Baumrucker | 128/DIG. 25 X |
| 3,903,894 | 9/1975 | Rosen et al. | 600/31 |
| 4,019,499 | 4/1977 | Fitzgerald | 600/30 |
| 4,786,276 | 11/1988 | Haber | 600/31 |
| 4,854,990 | 4/1986 | Haber et al. | 128/DIG. 25 X |

FOREIGN PATENT DOCUMENTS

37891/85 10/1988 Australia.

Primary Examiner—David H. Willse
Attorney, Agent, or Firm—Pennie & Edmonds

[57] ABSTRACT

A prosthetic anal sphincter is described which is implantable around the upper anal canal to reproduce the action of the sphincter muscles which maintain continence. This is achieved by inflating a tube with liquid from a reservoir and creating an angle of about 90° between the rectum and the anal canal and by flattening the upper anal canal by squeezing the posterior wall of anal canal against the anterior wall.

10 Claims, 2 Drawing Sheets

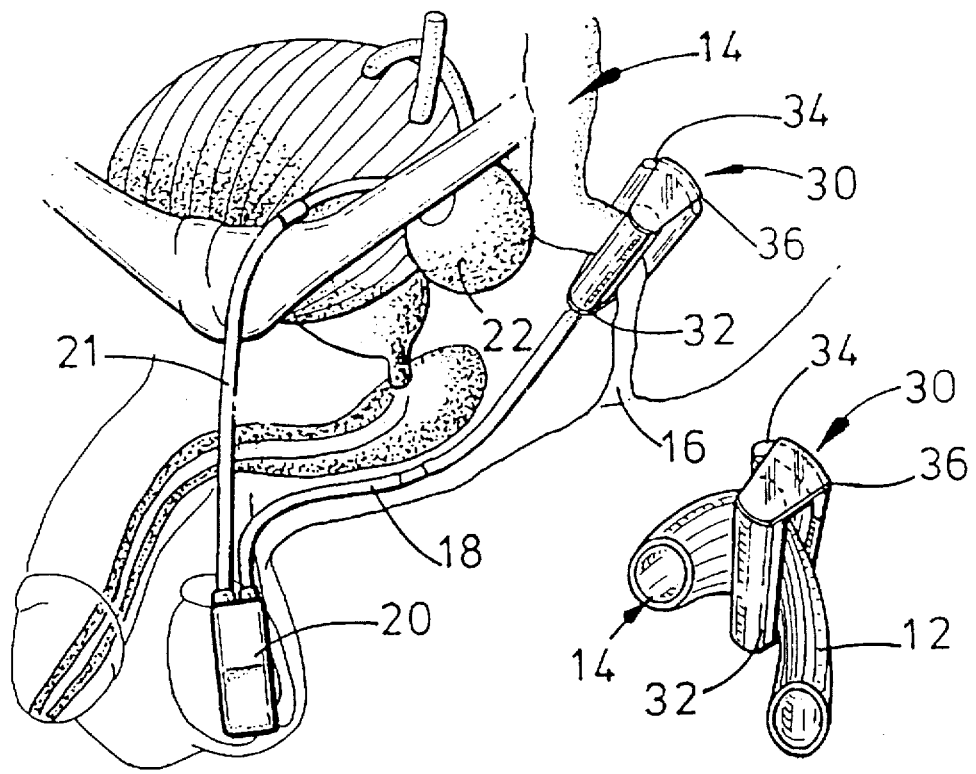
FIG.1
FIG.2
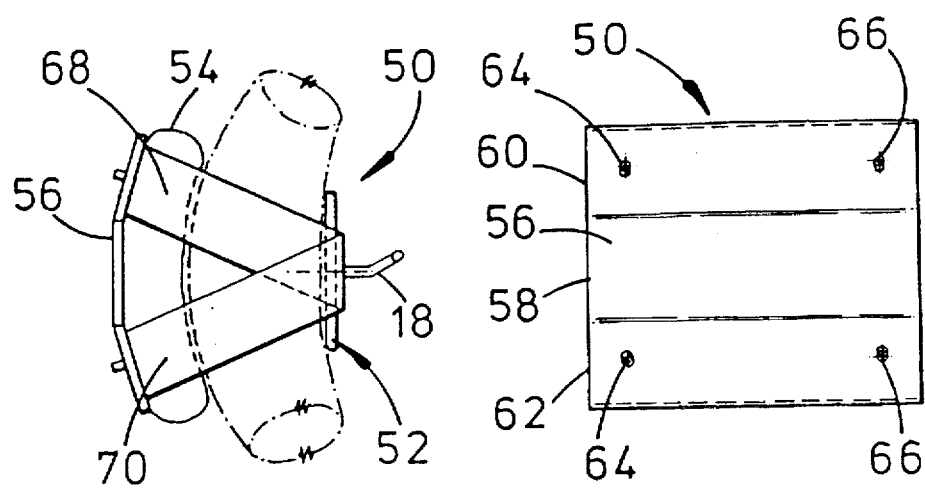
FIG.3
FIG.4

PROSTHETIC ANAL SPHINCTER

This is a continuation of application Ser. No. 08/117,181, filed as PCT/GB92/00349 Feb. 24, 1992, now abandoned.

The present invention relates to the treatment of incontinence and particularly, but not exclusively, to the treatment of faecal incontinence. In particular, the invention relates to a prosthetic anal sphincter which is under the voluntary control of the patient to control faecal excretion.

The natural mechanisms for controlling incontinence in human or animal bodies include occlusive rings of muscle at the outlets of the bladder and rectum. These sphincters are under both reflex and voluntary control. Urinary and faecal incontinence can occur when these sphincteric structures are damaged or rendered incompetent through a variety of causes. Faecal incontinence is a particularly distressing condition caused by failure of the anal sphincter to retain the contents of the rectum.

The use of an artificial sphincter to overcome incontinence was originated by Foley in 1947 who used such an artificial sphincter to treat urinary incontinence. The Foley artificial urinary sphincter (AUS) was simple in design and operation and depended on an inflatable cuff wrapped around the penile urethra and controlled by an air pump carried in the trouser pocket. More recently, a totally implantable AUS based on the Foley principle has been tried (Rosen, M (1976)., A simple Artificial Implantable Sphincter. Journal of Urology, 48, pp 675–680). The Rosen prosthesis comprises a silicone rubber occluder cuff which is disposed around the urethra and is attached via a tube to a rubber bulb and release valve which is placed in the scrotum. The system is filled with isotonic hydraulic fluid. This is a volume dependent device and consequently it suffers from the inherent deficiency that the pressure within the urethral occluder is not controlled or monitored and can be sufficiently high so as to cause excessive urethral compression with consequent tissue necrosis and cuff induced erosion. For this reason volume control sphincters have generally had a poor success rate and have not gained favour with most urological surgeons.

To overcome the problems with the Rosen prosthesis a pressure controlled inflatable artificial sphincter was developed as disclosed in U.S. Pat. No. 4,222,377 to Burton. This device was first implanted by Scott and is known as the Brantley-Scott prosthesis. (Scott et al, 1981. Implantation of an Artificial Sphincter for Urinary Incontinence. Contemp. Surg., 18, 11–14). The original product has undergone a number of modifications which has resulted in a simple design model which has been successfully exploited by American Medical Systems to control urinary incontinence and is known as the model AMS Sphincter 800. In the successful implementation of this inflatable artificial sphincter pressure control, delayed activation and automatic reinflation of the urethral cuff are incorporated in the product. The pressure control mechanism in this device relies on a silicone balloon inflated to the plateau where pressure is maintained independent of volume. Deflation of the cuff for voiding is achieved by squeezing a pump sited in the scrotum or labia. In a recent study on these AUS devices implanted into both men and women, it was concluded that they provide a "successful method of treatment for sphincter weakness incontinence regardless of aetiology" (Mundy & Nurse, 1988. One Hundred Artificial Sphincters. Brit Journal of Urol, 61, 318–325). In this study the conclusion is prefaced with a list of problems which are intrinsic to the AMS sphincter 800, namely that the control pressure cannot be altered without further surgery to replace the fixed pressure balloon; the device cannot rapidly increase cuff pressure in response to surges in abdominal pressure as would be necessary to prevent stress incontinence which is stated as being a particular problem when the cuff is placed in the bulbar urethral position and the pump, for deflating the cuff, is not easy to use, and some women find it distasteful to manipulate their labium in order to void, particularly if they get their hands wet in the process.

In a recent study (Christiansen, J and Lorentzen, M. Implantation of Artificial Sphincter For Anal Incontinence, a report of five cases Dis. Col. & Rect. 32; 5. 432–36, 1989.) the implantation of an artificial anal sphincter in five patients with anal incontinence of neuromuscular origin was described. The prosthesis used was the American Medical Systems AMS Sphincter 800 artificial urinary sphincter and this is reported as working well with solid or semi-solid stools but less satisfactorily when diarrhoea was present. In this study it was reported that it was appropriate if the inflated cuff could produce an anal canal pressure of approximately 80 mm Hg to ensure continence. However, it is believed that continued or prolonged anal canal-occlusion at pressures of this magnitude will occlude the vascular supply to the anal canal and lead to ischaemic necrosis.

In a very recent study by Craggs, M. D. ((1986) An Adjustable Pressure Regulated Artificial Urinary Sphincter, Journal of Physiology, 377, 6P) an adjustable pressure-regulated artificial urinary sphincter was designed to overcome problems associated with hitherto previous devices including the AMS Sphincter 800. This device is a more complex structure than the AMS Sphincter 800 and the principle advantage claimed is that adjustment to pressure may be made by injecting or withdrawing fluid through a hypodermic needle to or from a pressure-regulating balloon via a self-sealing filling port which is situated in the control part of the prosthesis implanted beneath the skin of the lower chest wall. In this paper, it is concluded that the results of the clinical tests have been disappointing with almost all the failures being attributed to mechanical problems. There is no disclosure in this paper of the device being applied to treat anal incontinence.

An object of the present invention is to provide an improved prosthetic anal sphincter which obviates or mitigates at least one of the aforementioned disadvantages associated with existing devices.

This is achieved by providing a prosthetic anal sphincter which is implanted around the upper anal canal to reproduce the action of the sphincter muscles which maintain continence. The prosthetic sphincter consists of an inflatable tube coupled to a liquid or gel filled bag which is substantially planar and non-inflatable, although in some embodiments liquid filled tubes inserted into the bag can be inflated to deform the bag. This is particularly achieved by inflating at least one tube with liquid from a reservoir and creating an angle about 90° between the rectum and the anal canal and by flattening the upper anal canal, in use, by squeezing the posterior wall of the anal canal against the the anterior wall. The bending of the anal canal to create an angle of about 90° is important as it creates a "flap valve" which resists the weight of solid faeces within the rectum whilst the flattening of the lumen of the canal produces a seal against the leakage of liquid or gas.

According to one aspect of the present invention there is provided a prosthetic anal sphincter for use with an artificial sphincter system, said prosthetic anal sphincter comprising:

a prosthetic anal sphincter for use with an artificial sphincter system, said prosthetic anal sphincter comprising:

a first inflatable prosthetic sphincter portion for disposing at one side of the anal canal, a second non-inflatable prosthetic sphincter portion for disposing at the other side of the anal canal said second non-inflatable prosthetic sphincter portion being provided by a bag permanently filled with liquid or gel which is mounted on a semi-flexible backing, the first and second prosthetic sphincter portions being adapted to be coupled together to form a structure to surround the anal canal at a location along its length, whereby said first and said second prosthetic sphincter portions are arranged so as to be disposed around the anal canal whereby, in use, when said first prosthetic sphincter portion is inflated, the lumen of the anal canal is flattened by being squeezed between said first inflatable sphincter portion and said liquid or gel filled bag to occlude the anal canal and provide a seal against the leakage of solids, liquid or gas and deflating of the first prosthetic portion releases pressure on the anal canal to allow the canal to open and facilitate defaecation.

Preferably, the liquid filled bag is concave to facilitate bending of the canal on inflation of the tube the bag having a first radius of curvature.

Preferably also the backing is sufficiently straight and long to allow the liquid filled bag to deform to define a second radius of curvature which is smaller than the first radius of curvature when the anal canal is squeezed against the bag by the inflated first sphincter portion.

Conveniently, the liquid or gel filled bag is provided with at least one additional liquid filled tube mounted on said semi-flexible backing, whereby when said at least one liquid filled tube is inflated, the angulation is augmented between said liquid or gel filled bag and said inflatable tube.

Preferably also, two additional liquid filled tubes are mounted inside the backing plate.

Conveniently, said liquid in said tubes is normal saline at a higher pressure than the liquid in said bag.

Advantageously, where said inflatable tubes are coupled to a variable volume reservoir by an implantable pump coupled thereto, said pump being actuatable by the patient to move fluid between the reservoir and the tubes to inflate and deflate the tubes.

The prosthetic anal sphincter may be used in combination with the existing AMS sphincter 800 system instead of the circular cuff which is unsuitable for use in occluding the anal canal. Consequently, deflation of the cylindrical tube in both of these embodiments is accomplished by the patient pumping liquid from the tubes into a spherical reservoir of variable volume using an implanted pump. Re-inflation requires the patient to activate a valve in the pump which allows the liquid from the spherical reservoir to be transferred to inflate the tube from the reservoir. This arrangement is already known and is disclosed in U.S. Pat. No. 4,222,377 to Burton.

According to the another aspect of the present invention there is provided a method of treating anal incontinence in a human or animal body comprising the steps of:

disposing a prosthetic anal sphincter around the anal canal so to form an angle of about 90° between the upper anal canal and the rectum, coupling the prosthetic anal sphincter to a patient-actuatable pump means to permit the patient to voluntarily control the operation of the prosthetic anal sphincter, in the absence of a voluntary input from the patient pressurising the prosthetic anal sphincter so as to squeeze the anterior and posterior walls of the anal canal together to occlude the lumen of the anal canal and create a fluid and solid resistant seal whereby, in use, actuation of the prosthetic anal sphincter pump means by the patient causes the prosthetic anal sphincter to deflate so that the anal canal is opened to permit defaecation.

Preferably, the tubular portion is inflated and the anal canal is occluded by compressing the anal canal against a non-inflatable semi-rigid portion to create a nip. Most preferably, the semi-rigid portion defines a concave surface to facilitate formation of the angle between the upper anal canal and the rectum. The semi-rigid portion includes a relatively flexible central part such that the portion deforms on inflation of the tubular portion to define a smaller radius curve.

Alternatively, a nip is created by disposing a liquid or gel filled substantially non-inflatable bag on one side of the anal canal and a single inflatable balloon member on the other side of the anal canal such that the balloon member is inflated, a nip is created such that the anal canal is flattened to occlude the lumen of the canal and to prevent leakage of solids, liquid or gas through the anal canal.

Preferably, the method includes the step of providing a feedback signal for indicating to the user when the pressure in the anal canal is sufficiently high to warrant actuation of the pump to facilitate defaecation. This is best implemented by a pressure sensor.

Preferably the method includes transiently providing increasing pressure in the prosthetic sphincter in response to a transient increase in intra-rectal pressure. This may be achieved by a fluid filled sensor connected to the rectum.

Preferably also, liquid or gel filled bag is coupled to at least one further liquid filled inflatable tube which, when inflated, augments the angulation between the inflatable tube and the liquid or gel filled bag.

These and other aspects of the present invention will become apparent from the following description when taken in combination with the accompanying drawings in which:

FIG. 1 depicts a diagrammatic view of an embodiment of a prosthetic anal sphincter in accordance with the present invention also shown fitted around the anal canal;

FIG. 2 is an enlarged view of the prosthetic anal sphincter shown in FIG. 1;

FIG. 3 is a side view of an alternative embodiment of a prosthetic anal sphincter in accordance with the present invention shown fitted around a portion of the anal canal;

FIG. 4 is an end view of the prosthetic anal sphincter of FIG. 3;

Figure 5:
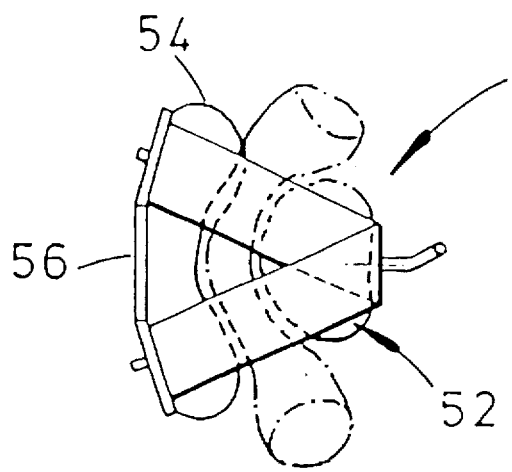
FIG. 5 is a side view of the prosthetic anal sphincter of FIG. 3, showing the sphincter configured to close the anal canal.

Reference is first made to FIGS. 1 and 2 of the drawings which depicts a prosthetic anal sphincter generally indicated by reference numeral 30 which is shown disposed around the upper anal canal 12 which connects rectum 14 to the anus 16. The prosthetic anal sphincter 30 is coupled via conduit 18, pump 20 and conduit 21 to a variable volume reservoir 22. As will be later described in detail the patient may actuate the pump 20 to cause the prosthetic anal sphincter to inflate and deflate as required to provide continence or defaecation as necessary.

The prosthetic anal sphincter 30 consists of essentially two parts; a first inflatable/deflatable liquid filled tube 32 which is coupled to the liquid conduit 18 and a second elongate portion which consists of a gel filled bag 34 mounted on an arcuate rigid or semi-flexible plastic backing 36 such that the gel filled bag adopts an arcuate or curved cross-section as best seen in FIG. 2. The liquid filled tube 32 and gel filled bag 34 are arranged so that they create an angle of approximately 90° in the lower anal canal which has been found, as a result of experiments carried out by Finlay et al (Brit. J. Surg. 1986, 73, p. 1025) to be extremely important in providing continence. The liquid filled tube 32 is generally parallel to the gel filled bag 34 such that when the liquid filled tube is inflated the anterior wall of the anal canal is flattened against the posterior wall so as to occlude the anal canal and to retain solid and liquid faeces and preventing the leakage of liquid and gas through the anal canal thus providing continence. The conduit 18, pump 20 and reservoir 22 are part of the AMS (American Medical Systems) Sphincter 800 prosthesis. The tubes and bag are made of a silicone material or other bio-compatible material and contain an isotonic radio opaque fluid of a type well known in the art and the tubes are arranged so that they are effectively parallel and when inflated, the tube squeezes the anal canal flat so as to occlude the lumen of the canal as the anterior canal wall is pressed against the posterior canal wall. This occlusion combined with the proximately 90° bend in the canal created by the prosthetic anal sphincter results in an arrangement which prevents leakage of solid, liquid faeces and perhaps gas through the anal canal thus providing continence.

The liquid filled tube 32 is coupled via conduit 18, pump 20 and conduit 21 to the variable volume reservoir 22. Once the artificial sphincter system has been installed surgically and the prosthetic anal sphincter is located around the anal canal 14 as shown, the prosthetic sphincter is oriented in-situ to create a substantially right-angled bend in the lower anal canal to facilitate control of faecal continence as described above. As is well known in the art, the system is set up such that in the absence of any voluntary input from the patient the pressure exerted by the reservoir via pump and valve 20 and conduit 18 is such that the liquid filled tube is inflated and presses against the anal canal such that the anterior wall is flattened against the posterior wall to occlude the lumen of the canal and provide continence. The pressure created by this arrangement is around 50 mm of mercury to minimise the possibility of ischaemic necrosis of the anal canal wall tissue due to prolonged pressure.

When the patient requires to defaecate he actuates the pump 20 to displace fluid from the tube 32 into the reservoir 22 which expands to accommodate the additional fluid. This relieves pressure on the anal canal which opens so that the lumen of the canal is patent and the patient is able to defaecate. After defaecation either fluid leaks back from reservoir 22 or the pateent activates a valve in the pump 20 which permits fluid to flow from reservoir 22 through conduit 18 to reinflate the tube 32, again occluding the anal canal and providing continence. The precise operation of the American Medical Systems sphincter 800 system is well known in the art and is disclosed in more detail in U.S. Pat. No. 4,222,377.

Reference is now made to FIGS. 3, 4 and 5 of the drawings which depicts an alternative embodiment of a prosthetic anal sphincter generally indicated by reference numeral 50. It will be understood that like numerals in this embodiment refer to like features described with reference to FIGS. 1 and 2.

Like the embodiment described with reference to FIGS. 1 and 2, the prosthetic anal sphincter 50 consists of essentially two parts; a first inflatable/deflatable liquid filled tube 52 which is coupled to the liquid conduit 18 and a second elongate portion which consists of a silicone gel filled bag 54 mounted on an arcuate backing 56 such that the gel filled bag adopts an arcuate or curved cross-section as best seen in FIG. 3. The liquid filled tube 52 is generally parallel to the gel filled bag 54 such that when the liquid tube is inflated the anterior wall of the anal canal is flattened against the posterior wall so as to occlude the anal canal thus retaining solid and liquid faeces and preventing the leakage through the anal canal to provide continence.

However, the backing 56 has the centre portion formed of 1 mm thick silicone rubber film, whereas the upper and lower portions 60, 62 are formed of stainless steel foil. Also, the wall of the gel filled bag 54 is flexible such that the bag 54 will be deformed by the inflated tube 52 as shown in FIG. 5 to reduce the radius of curvature of the wall of the bag 54 and thus of the canal. When the tube 52 is deflated by the patient, the stored energy in the wall of the bag 54 and the backing 56 return the bag 54 to the less steeply curved form and the lumen of the anal canal is free to become patent, as it will under the influence of intra-abdominal pressure forces.

Mounted on each upper and lower portion 60, 62 are two fixing hooks 64, 66 which provide attachment for flexible fixing straps 68, 70 used to connect the tube 52 and bag 54.

This arrangement tends to increase the angle which the anal canal is turned through by the sphincter and also closes the anal canal over a larger area, thus reducing the tube pressure necessary to provide continence.

Figure 6:
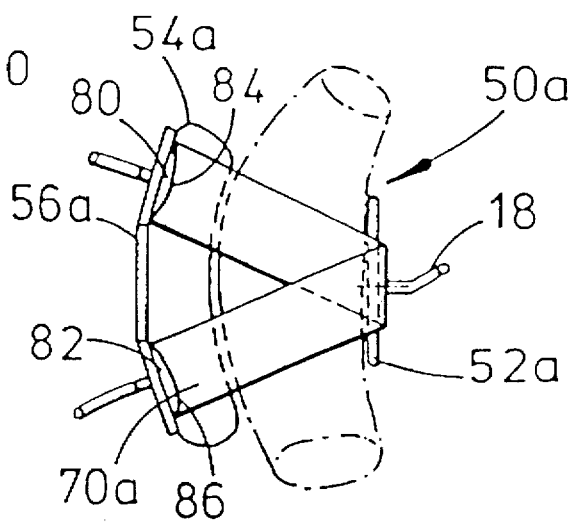
FIGS. 6, 7 and 8 are diagrammatic views of the embodiment shown in FIGS. 3 to 5 with the addition of tubes which can be inflated with liquid to increase the degree of angulation.
Figure 7:
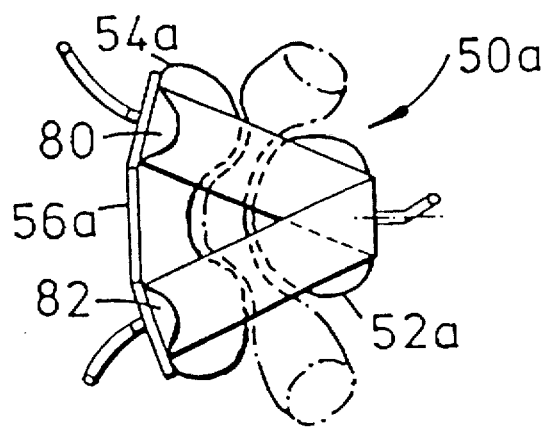
Figure 8:
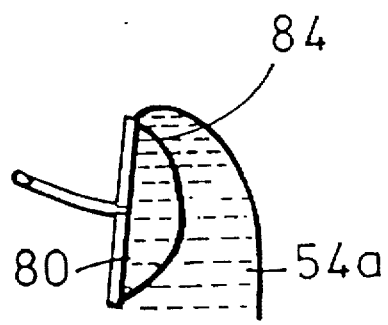

A further embodiment is shown in FIGS. 6, 7 and 8 of the drawings which is similar to that shown in FIG. 3, and in which like numerals denote like parts with the suffix "a" added, except that two additional liquid filled tubes 80,82 are mounted onto the backing 56a. When these tubes are inflated, as shown in FIG. 7, they exert pressure against the gel filled bag 54a to augment the angulation achieved when the central tube 52a is inflated. The inflatable tubes 80,82 are connected to a reservoir 22a and to a single pump 20a so that during evacuation all three tubes are deflated.

The gel in the bag may be replaced by a liquid, for example, normal saline. In this case a thinner wall 84,86 of silicone rubber may be used to assist saline from the pressurised tubes 80,82 diffusing through to the bag 54 due to a pressure differential. This is to compensate for the inevitable loss of liquid from a sealed bag due to diffusion over a prolonged period.

It will be appreciated that various modifications may be made to the embodiments of the prosthetic anal sphincter hereinbefore described without departing from the scope of the invention. It will be appreciated that although the material used to create the liquid filled tubes is described as being silicone, any other suitable bio-compatible material may be used. Furthermore, the shape and structure of the anal sphincter need not be exactly as described in the embodiments. The important thing is to occlude the tube by flattening the tube rather than by compressing it circumferentially as has been done with the AMS 800 artificial urinary sphincter. Such compression causes the anal canal to fold and is very much harder to occlude with the result that incontinence may still occur. The pressure then necessary to obtain satisfactory occlusion are of a level such that ischaemic necrosis of the anal canal tissue with erosion of the sphincter into the anal canal is a real possibility. Accordingly, the structure of the sphincter should be such that there is one member which presses across the width of the tube against another member to flatten the tube and it will be appreciated that structures in accordance with such a concept can take many forms, although only two such structures are described herein. It will also be appreciated that although the prosthetic anal sphincter is described as being connected to the AMS 800 artificial sphincter control system, it will be appreciated that any other suitable control system may be used which can be actuated to inflate and deflate the prosthetic artificial sphincter to control continence.

It will be understood that the pump and suitable directional valves may be configured so that the patient manually deflates and inflates the occluding tubes, (or balloon). Alternatively, the pump includes a valve which is actuatable by the patient to allow liquid to be transferred back to the balloon from the reservoir to re-inflate the balloon to occlude the anal canal. It will also be appreciated that the pump may be mechanical or electrical for voluntary actuation.

The principal advantage of the invention is that there is provided a relatively simple structure which can be readily and surgically installed and which can be operated with the existing apparatus to provide satisfactory faecal continence. The design of the structure creates a substantially right-angled bend in the upper anal canal which together with the fact that occlusion is created by pressing the anal canal flat across its width minimises the level of pressure required to achieve occlusion of the lumen of the anal canal thus minimising the possibility of ischaemic necrosis of the anal canal occurring. A further advantage of the prosthetic anal sphincter is that is can be readily coupled to an existing sphincter control system which has been successfully installed in patients and received generally widespread medical acceptance in the treatment of urinary incontinence.

We claim:

1. A prosthetic anal sphincter for use with an artificial sphincter system, said prosthetic anal sphincter comprising:

a first inflatable prosthetic sphincter portion for disposing at one side of an anal canal;

a second non-inflatable prosthetic sphincter portion for disposing at the other side of the anal canal, said second portion comprising a bag mounted on a rigid or semi-flexible backing, said bag being at least as wide as the first portion and being filled with a liquid or gel;

the first and second portions configured to be connected together to form a structure to surround the anal canal at a location along its length in which said first portion is disposed opposite a central area of said bag;

wherein when said first portion is inflated, the anal canal is squeezed between said first portion and said bag, the backing provides a reaction force against said bag to augment angulation between said bag and said first portion to form a bend in the anal canal, and a lumen of the anal canal is flattened, occluding the anal canal and providing a seal against the leakage of solids, liquid or gas; and wherein when said first portion is deflated, the backing no longer provides the reaction force against said bag and pressure on the anal canal is released, allowing the canal to open and facilitate defecation.

2. A sphincter as claimed in claim 1 wherein the bag is concave to facilitate bending of the canal on inflation of the first inflatable prosthetic sphincter portion, the bag having a first radius of curvature when said first portion is not inflated.

3. A sphincter as claimed in claim 2 wherein the backing is sufficiently straight and long to allow the bag to deform to define a second radius of curvature which is smaller than the first radius of curvature when the anal canal is squeezed against the central area of the bag when said first portion is inflated.

4. A sphincter as claimed in claim 3 wherein said first portion is an inflatable tube which, when inflated, has a substantially circular cross-section.

5. A sphincter as claimed in claim 1 wherein, when said first portion is inflated, a substantially right-angled bend is formed in the anal canal.

6. A prosthetic anal sphincter comprising:

an inflatable tube for disposing at one side of an anal canal;

a prosthetic sphincter portion for disposing at the other side of the anal canal, said spincter portion comprising a bag mounted on a rigid or semi-flexible backing, said bag being at least as wide as the inflatable tube and being filled with a liquid or gel;

the inflatable tube and said spincter portion configured to be connected together to form a structure to surround the anal canal at a location along its length in which the inflatable tube is disposed opposite a central area of said bag and wherein said bag is provided with at least one additional liquid filled tube mounted on said backing, whereby when said at least one additional liquid filled tube is inflated, angulation between said bag and said inflatable tube is augmented.

7. A sphincter as claimed in claim 6 wherein two additional liquid filled tubes are mounted on the backing.

8. A sphincter as claimed in claim 7 wherein said liquid in said additional liquid filled tubes is saline at a higher pressure than the liquid or gel in said bag.

9. A sphincter as claimed in claim 8 wherein said inflatable tube and said additional liquid filled tubes are coupled to a variable volume reservoir by an implantable pump coupled thereto to provide an artificial sphincter system, said pump being actuable by the patient to move fluid between the reservoir and the tubes to inflate and deflate the tubes.

10. A prosthetic anal sphincter comprising:

an inflatable tube for disposing at one side of an anal canal, said tube having a substantially circular cross-section when inflated;

a prosthetic sphincter portion for disposing at the other side of the anal canal, said spincter portion comprising a concave bag at least as wide as said inflatable tube and mounted on a rigid or semi-flexible backing;

the inflatable tube and said spincter portion configured to be connected together to form a structure to surround the anal canal at a location along its length in which the inflatable tube is disposed opposite a central area of said bag;

the bag being filled with liquid or gel and having a first radius of curvature when the inflatable tube is not inflated and said concavity of the bag facilitating a bending of the canal when said inflatable tube is inflated;

the backing being sufficiently straight and long to allow the bag to deform to define a second radius of curvature smaller than the first radius of curvature when the canal is squeezed against a central area of the bag upon inflating said inflatable tube; and wherein said bag is provided with at least one additional liquid filled tube mounted on said backing, whereby when said at least one additional liquid filled tube is inflated, angulation between said bag and said inflatable tube is augmented.

* * * * *